United States Patent [19]

Castellana et al.

[11] Patent Number: 5,074,852
[45] Date of Patent: Dec. 24, 1991

[54] OCCLUSIVE ATTACHING DEVICE FOR OSTOMY APPLIANCE

[75] Inventors: Frank S. Castellana, Princeton; Thomas A. Iliadis, Freehold, both of N.J.; Walter F. Leise, Yardley, Pa.; Keith T. Ferguson, Scotch Plains, N.J.

[73] Assignee: E. R. Squibb & Sons, Inc., Princeton, N.J.

[21] Appl. No.: 394,619

[22] Filed: Aug. 16, 1989

[51] Int. Cl.$^5$ .............................................. A61F 5/44
[52] U.S. Cl. ...................................... 604/336; 604/344
[58] Field of Search ................ 604/332, 336, 343, 344

[56] References Cited

U.S. PATENT DOCUMENTS

| | | | |
|---|---|---|---|
| 3,339,546 | 9/1967 | Chen | 128/156 |
| 4,192,785 | 3/1980 | Chen et al. | 260/17.4 GC |
| 4,204,540 | 5/1980 | Cilento et al. | 604/336 |
| 4,213,458 | 7/1980 | Nolan et al. | 128/283 |
| 4,253,460 | 3/1981 | Chen et al. | 604/336 |
| 4,393,080 | 7/1983 | Pawelchak et al. | 428/355 |
| 4,419,100 | 12/1983 | Alexander | 604/339 |
| 4,460,363 | 7/1984 | Steer et al. | 604/336 |
| 4,490,145 | 12/1984 | Campbell | 604/333 |
| 4,551,490 | 11/1985 | Doyle et al. | 524/22 |
| 4,775,374 | 10/1988 | Cilento et al. | 604/344 |

FOREIGN PATENT DOCUMENTS 264299 4/1988 European Pat. Off. .

Primary Examiner—Ronald Frinks
Assistant Examiner—R. Clarke
Attorney, Agent, or Firm—Richard H. Brink; Stephen B. Davis

[57] ABSTRACT

Occlusive attaching means comprising a first relatively thick adhesive component to be secured to the skin around the stoma and a relatively thin flexible second adhesive component to be secured to the skin at a distance from the stoma. Both adhesive components include an occlusive adhesive layer formulated as a blend containing one or more water soluble or swellable hydrocolloids dispersed in polyisobutylene along with other optional ingredients. The attaching means can be utilized as part of a one or two-piece ostomy system.

14 Claims, 3 Drawing Sheets

OCCLUSIVE ATTACHING DEVICE FOR OSTOMY APPLIANCE

BACKGROUND OF THE INVENTION

Cilento et al. U.S. Pat. No. 4,775,374 disclose a two piece ostomy system in which the body side is a composite of a first adhesive component which contacts the skin adjacent the stoma, a coupling element, and a second adhesive component which is thin and flexible in comparison to the first adhesive component and has a degree of porosity. The second adhesive component contacts the skin at a distance from the stoma.

Alexander U.S. Pat. No. 4,419,100 discloses a two piece ostomy system in which the body side includes a resilient sealing ring 32 of any pliable and tacky material capable of sealingly engaging the peristomal area secured to gas-permeable water resistant microporous backing 30. A portion of the backing 30 extends beyond sealing ring 32 and is coated with a layer of pressure sensitive microporous adhesive.

Campbell U.S. Pat. No. 4,490,145 discloses a one-piece ostomy pouch in which the adhesive attaching means comprises a ring of a non-porous hydrocolloid containing adhesive of 10 to 30 mils attached to a tape of 2 to 3 mils. The tape consists of a microporous adhesive and a breathable non-woven backing.

Samuelsen in European Patent Application 264,299 discloses a hydrocolloid containing adhesive skin barrier or sealing pad which can be employed as the attaching means for an ostomy pouch. The outer periphery of the sealing pad is bevelled such that its thickness adjacent its outer edge does not exceed about one quarter of the thickness of its non-bevelled region.

SUMMARY OF THE INVENTION

This invention is directed to an adhesive attaching means for securing an ostomy appliance to the body of the user. The attaching means comprises a relatively thick first adhesive component adapted to be secured to the skin around the stoma and a relatively thin flexible second adhesive component adapted to be secured to the skin at a distance from the stoma. Unlike the prior art composite devices discussed above, both adhesive components include an occlusive adhesive layer formulated as a blend containing one or more water soluble or swellable hydrocolloids dispersed in polyisobutylene along with other optional ingredients. A backing layer comprising a thin polymeric film or a non-woven fabric material is included in the second adhesive component and a thin polymeric film may also be included in the first adhesive component.

The occlusive attaching means of this invention can be employed as the skin barrier portion of a two-piece ostomy system. In this embodiment, a bodyside coupling member, for example, of the type described by Steer et al. U.S. Pat. No. 4,460,363 and Cilento et al. U.S. Pat. No. 4,775,374 is employed to which the coupling member of an ostomy pouch can be coupled and decoupled when desired. The flange skirt of the body side coupling can be affixed to the thin polymeric backing film on the relatively thick first adhesive component and then the relatively thin, flexible second adhesive component can be secured to the opposite surface of the flange skirt. In this embodiment the backing layer can be either the polymeric film or the non-woven fabric. Alternatively, the second adhesive component can be secured directly to the first adhesive component or directly to the first adhesive layer and the coupling member flange skirt can then be secured to the thin polymeric film on the second adhesive component.

The occlusive attaching means of this invention can also be employed as part of a one-piece ostomy pouch. In this embodiment, the second relatively thin adhesive component can be secured to the relatively thick first adhesive component or directly to the thick first adhesive layer and then the thin polymeric backing film on the second adhesive component can be secured to the ostomy pouch in the area around the pouch stomal aperture. Alternatively, the thin polymeric film on the relatively thick first adhesive component can be secured to the ostomy pouch in the area around the pouch stomal aperture but leaving an outer periphery of the first component unsecured to the pouch. The relatively thin, flexible second adhesive component is secured to this peripheral portion of the first component backing film. In this embodiment the backing layer can be either the polymeric film or the non-woven fabric.

This invention is also directed to an improved process for securing the relatively thick first adhesive component to the relatively thin, flexible second adhesive component. As a result of this process both adhesive surface can be protected prior to use by a single sheet of release paper. This provides added convenience to the user in securing the occlusive attaching means to the peristomal area.

DETAILED DESCRIPTION OF THE INVENTION

Figure 1:
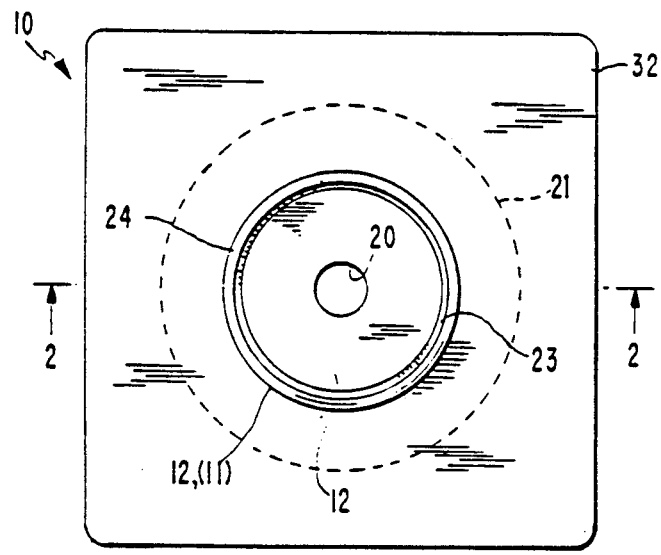
FIG. 1 is a top view showing the occlusive attaching means of this invention as the skin barrier of a two-piece ostomy system.

This invention is directed to an adhesive attaching means which can be employed as part of either a one or two-piece ostomy appliance. The adhesive attaching means comprises a first adhesive component including a first adhesive layer which contacts the skin in the area immediately surrounding the user's stoma known as the peristomal area and a second adhesive component including a second adhesive layer which is attached to the skin at a distance from the stoma.

Unlike prior adhesive systems, both the first and second adhesive layers of the attaching means of this invention are occlusive and are formulated from materials which retain their ability to adhere to the skin in the presence of moisture or fluids which can leak from the stoma. By employing an occlusive formula for the adhesive layer of the second adhesive component of the attaching means of this invention, the overall product has increased moisture resistance. Thus, fluids which may erode or tunnel through the adhesive layer of the first component are contained by the occlusive adhesive layer of second component resulting in improved wear time for the user. Additionally, by employing skin friendly non-acrylic materials in both the first and second adhesive layers, the overall product is less irritating to the skin even though the adhesive layers are occlusive. The overall occlusive attaching means of this invention is more extensible and conformable to the body contours of the user and thus in use is more comfortable for the user.

Relatively thick first adhesive layer 11 and relatively thin second adhesive layer 31 are both formulated as occlusive adhesive layers by blending one or more water soluble or swellable hydrocolloids with a polyisobutylene or a mixture of polyisobutylenes or a mixture of one or more polyisobutylenes and one or more non-acrylic elastomers. Other materials can be included within the adhesive formulations such as mineral oil, tackifiers, antioxidants, cohesive strengthening agents, and pharmaceutically active materials such as antiinflammatory agents, antiseptics, or materials having skin healing or soothing properties. Suitable occlusive adhesive formulations are taught by Chen U.S. Pat. No. 3,339,546, Chen et al. U.S. Pat. No. 4,192,785, Pawelchak et al U.S. Pat. No. 4,393,080, Doyle et al. U.S. Pat. No. 4,551,490, and by Keyes et al. U.S. Pat. No. 4,762,738. As disclosed in these references, suitable water soluble and water swellable hydrocolloids include sodium carboxymethylcellulose, pectin, gelatin, guar gum, locust bean gum, gum karaya, and mixtures thereof. Suitable cohesive strengthening agents include water-insoluble cross-linked sodium carboxymethylcellulose, water-insoluble cross-linked dextran, etc. Suitable non-acrylic elastomers include butyl rubber and styrene radial or block copolymers such as styrene-butadiene-styrene (S-B-S) and styrene-isoprenestyrene (S-I-S) block type copolymers.

First adhesive component A includes a relatively thick first adhesive layer 11. Adhesive layer 11 by virtue of its ability to adhere to moist skin surfaces functions to secure the appliance to body and also to seal and protect the peristomal skin from bodily fluids which may leak from the stoma and not flow into the collection pouch. Adhesive layer 11 is about 40 to about 100 mils thick, preferably about 60 to about 80 mils thick, and most preferably about 70 mils thick. First adhesive component A may also include a polymeric backing film 12 coextensive with adhesive layer 11. Backing film 12, if present, is about 1 to about 4 mils in thickness. Adhesive component A includes a centrally located aperture 20 sized to fit around the stoma of the user or which functions as a starter hole that the user enlarges so as to fit around the stoma.

Second adhesive component C includes a relatively thin adhesive layer 31 and a backing layer 32. Depending upon the particular embodiment, backing layer 32 comprises a thin polymeric film or a non-woven fabric. Adhesive 31 is about 8 to about 20 mils, preferably about 10 to about 12 mils, in thickness and backing layer 32 is about 1 to about 4 mils in thickness.

Suitable materials for thin polymeric films 12 and 32 include the various materials commonly employed in ostomy and medical devices. For example, polyolefins such as polyethylene, embossed polyethylene and polypropylene, ethylene acrylic acids, ethylene vinyl acetates, polyvinylchlorides, polyether sulfones, polyether ketones, polyether urethanes, polyurethanes, etc.

Suitable non-woven fabrics which can be employed as backing layer 32 include those made from polyester fibers, polypropylene fibers, nylon fibers, composite olefin fibers, or cellulose fibers.

Figure 2:
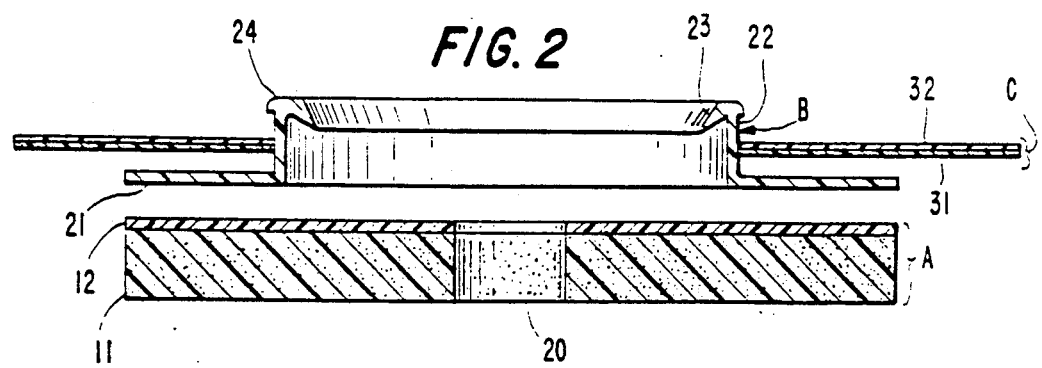
FIG. 2 is an exploded front view of the composite skin barrier taken along line 2—2 of FIG. 1 in greatly enlarged detail.
Figure 3:
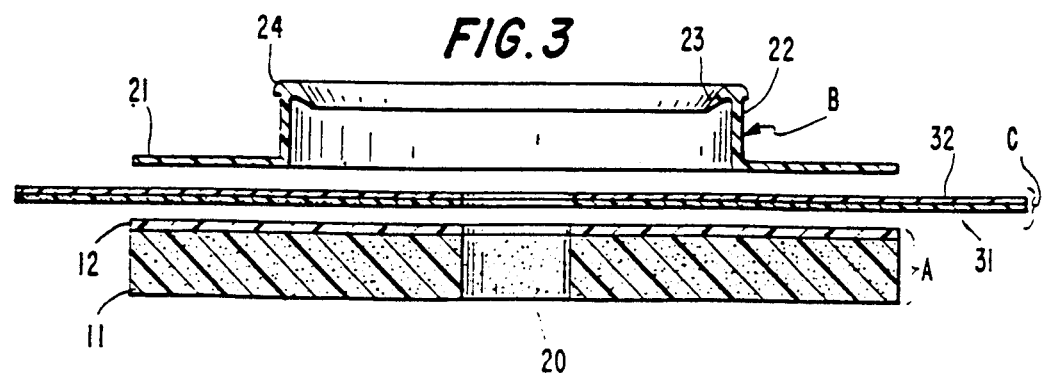
FIG. 3 is an exploded front view similar to FIG. 2 of an alternate embodiment employing the occlusive attaching means of this invention as the skin barrier of a two-piece ostomy system.

FIGS. 1 to 3 show two different embodiments in which the occlusive attaching means of this invention is utilized as the body side of a two piece coupling system. In FIGS. 1 and 2, first adhesive component A comprises relatively thick first adhesive layer 11 and thin polymeric backing film 12 with a centrally located aperture 20. A male coupling member molded as a single part of polyethylene including a skirt 21, upstanding rib 22, deflectable sealing strip 23, and rim 24 as taught by Steer et al. U.S. Pat. No. 4,460,363 and Cilento et al. U.S. Pat. No. 4,775,374 is affixed to backing film 12 by ultrasonically welding, heat sealing, or adhesively securing the bottom of skirt 21 to the top of film 12. Second adhesive component C is dimensioned to extend from rib 22 outwardly beyond the borders of component A and is secured to the top surface of skirt 21. This bond is adhesive in nature and may be augmented or supplemented if needed by the use of heat and pressure or by corona treating the top surface of skirt 21 as is well known in the plastics art.

FIG. 3 shows an alternative construction of the body side in which adhesive layer 31 of component C is attached directly to the backing film 12 of component A. Component C in this embodiment also includes an aperture 20 and is dimensioned to cover and extend beyond the periphery of component A. Skirt 21 of the male coupling member is then secured directly to polymeric backing film 32 of component C by the means described above. If layer 32 is a non-woven fabric, then the skirt would be adhesively secured to layer 32.

It should be appreciated that in either of these embodiments, polymeric film 12 could be omitted in which instance component A would consist only of adhesive layer 11.

Prior to use, the exposed adhesive surfaces of layers 11 and 31 would be covered by a sheet of protective material preferably silicone coated release paper. The embodiment of FIGS. 1 and 2 would employ two separate sheets which could be slitted for easier removal. As will be explained in more detail below, the embodiment shown in FIG. 3 could employ a single sheet of release paper over both adhesive surfaces 11 and 31.

The outer rectangular periphery shown for component C and the circular periphery shown for sealing skirt 21 and component A can be varied if desired. Of course, a closed ended or drainable ostomy pouch provided with a channel shaped coupling member as taught by Steer et al. in U.S. Pat. No. 4,460,363 is utilized with the body side of FIGS. 1 to 3. The channel is dimensioned to receive rib 22 and deflect strip 23 into a gas tight fit. The channel can also include a complimentary surface for rim 24. The details of the male coupling member are shown merely for exemplatory purposes and form no part of this invention.

Figure 4:
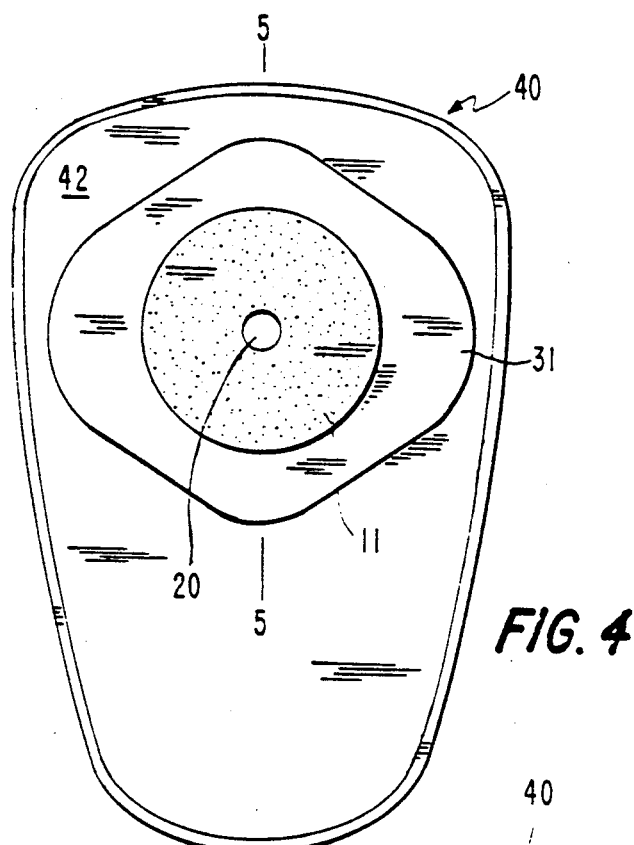
FIG. 4 is a front view showing the occlusive attaching means of this invention employed as part of a one-piece ostomy pouch.
Figure 5:
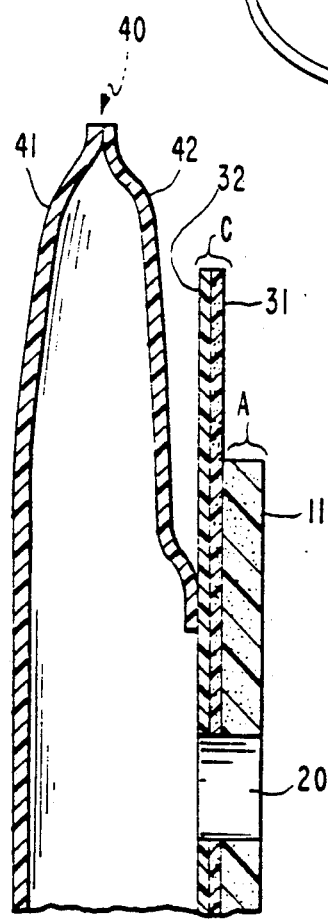
FIG. 5 is a side view along the line 5—5 of FIG. 4 through the occlusive attaching means.
Figure 6:
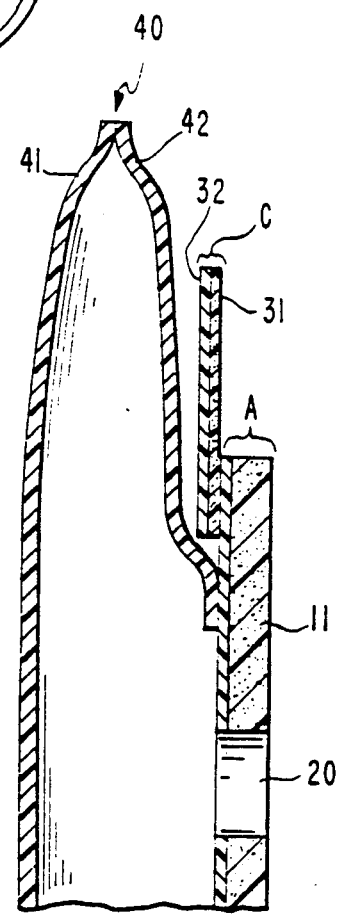
FIG. 6 is a side view similar to FIG. 5 showing an alternate manner of utilizing the occlusive attaching means of this invention in a one-piece ostomy pouch.

FIGS. 4 to 6 show the occlusive attaching means of this invention utilized as part of a one-piece ostomy appliance. As shown in FIGS. 4 and 5, the one piece appliance 40 consists of panels 41 and 42 sealed around their periphery. Panel 42 includes an opening through which the stoma can protrude. While pouch 40 is shown as being closed ended as commonly utilized by a colostomy patient, a similar pouch having a drainable tail portion closed by a clip as commonly utilized by an ileostomy patient or a drain valve as commonly utilized by a urostomy patient could be employed.

The occlusive attaching means shown in FIGS. 4 and 5 consists of first adhesive component A and second adhesive component C. Adhesive component A is the relativley thick occlusive adhesive layer 11 and adhesive component C is the relatively thin occlusive adhesive layer 31 with a thin polymeric film as backing layer 32. Adhesive layer 11 is bonded directly to adhesive layer 31 and a stomal aperture 20 through adhesive layers 11 and 31 and backing layer 32 is provided. Stomal aperture 20 is smaller than the stomal aperture in pouch panel 42 and a portion of backing layer 32 of component C is bonded to panel 42 around the panel aperture. The bond between polymeric film backing layer 32 and panel 42 is normally made by conventional heat sealing techniques though other types of bonding such as RF welding or the use of adhesives could be employed. In this embodiment, component A is shown without backing layer 12. However, such a backing layer could be included in which case adhesive layer 31 would be bonded to backing layer 12 similar to the construction shown in FIG. 3.

In the one-piece embodiment shown in FIG. 6, component A includes relatively thick occlusive adhesive layer 11 and a polymeric backing film 12 provided with a stomal aperture 20. A portion of polymeric backing film 12 is bonded to panel 42 by the techniques described above. Component C is bonded to the portion of component A unattached to panel 42 by the adhesive bond between relatively thin adhesive layer 31 and polymeric backing film 12. In this embodiment, backing layer 32 of component C could be either a thin polymeric film or a non-woven fabric.

In both of the one and two piece embodiments, component C extends outwardly beyond the border of component A so that adhesive layer 31 contacts the body of the user at a distance from the stoma. By virtue of the occlusive nature of adhesive layer 31, stomal exudate that channels or erodes through a portion of adhesive layer 11 is absorbed by layer 31 which retains its adhesiveness in the presence of such materials. As a result, the useful life of the appliance on the user is increased while retaining the benefit of increased flexibility and comfort resulting from the use of relatively thin adhesive layer 31. Also, since adhesive layer 31 is formulated from the same skin friendly materials as adhesive layer 11, repeated removal and application is less irritating than the prior systems where layer 31 was an acrylic adhesive.

Figure 7:
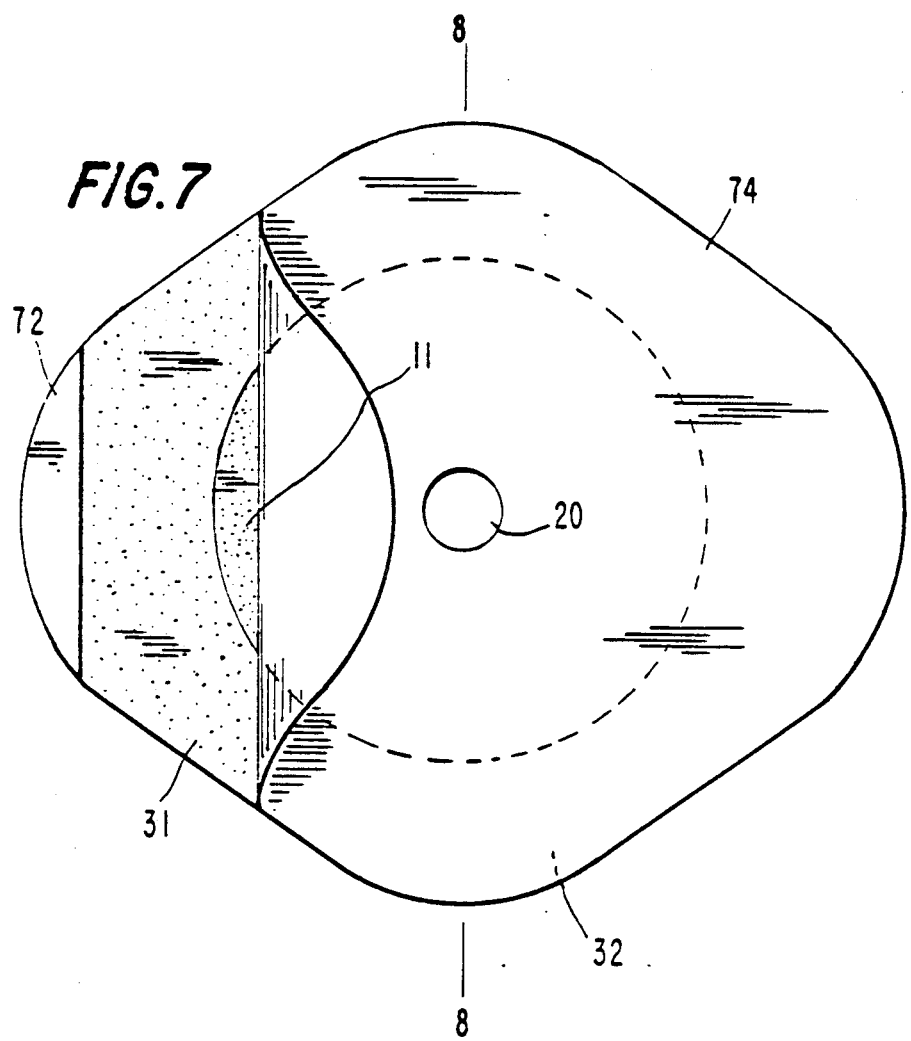
FIG. 7 is a view of the occlusive attaching means prepared by the improved process with the release paper partially removed.
Figure 8:
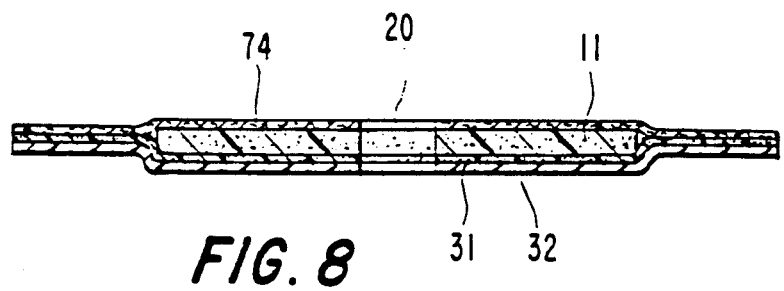
FIG. 8 is a side view taken along line 8—8 of FIG. 7.

FIGS. 7 and 8 show the occlusive attaching means of this invention made by a preferred process. This preferred process is suitable for preparing the occlusive attaching means for use as the body side of a two-piece appliance as shown in FIG. 3 and for the one-piece appliance construction shown in FIGS. 4 and 5.

According to this improved process, the adhesive mass of relatively thick adhesive layer 11 is prepared in the usual manner. The polyisobutylene, hydrocolloid powders, and other ingredients are blended with heating in a suitable mixer such as a sigma blade mixer until homogeneous. This mass is extruded to the desired thickness onto a sheet of silicone coated release paper. If backing film layer 12 is included as part of component A, then a sheet of polymeric film material 12 is laminated to the other surface of adhesive 11. If backing layer 12 is not included, then a second sheet of release paper is laminated to the other surface of adhesive 11. Similarly, the adhesive mass of relatively thin adhesive layer 31 is prepared, extruded to the desired thickness, and laminated between backing layer material 32 and release paper to form component C.

The release paper is removed from a sheet of component C. A wafer of component A is cut to the desired shape, such as the circular shape shown in the figures. If component A includes the backing film layer 12, then the single sheet of release paper is removed from adhesive surface 11 and backing film layer 12 of componenet A is applied to adhesive layer 31 of component C. If component A does not include a backing film layer 12, then both sheets of release paper are removed from adhesive layer 11 and layer 11 is applied to adhesive layer 31 of component C.

In the next step of the process, a strip of release paper 72 is applied to one corner of adhesive layer 31 and a second sheet of release paper 74 is applied over both adhesive layers 11 and 31 as well as strip 72. This assembly is then placed within a vacuum chamber and a vacuum is drawn removing the air from between layers 31 and backing layer 12 or adhesive layer 11 if there is no backing layer 12 and also removing the air from between the release paper 74 and the adhesive layers 11 and 31. Release of the vacuum draws adhesive component A into intimate contact with component C to the extent that component A deforms the surface of component C reducing the height differential between surfaces 31 and 11. This enables the single sheet of release paper 74 to form a tight bond with both adhesive surfaces.

This assembly is then removed from the vacuum chamber and stomal aperture 20 and the outline cut are made. The outline cut can, for example, be rectagular as shown in FIG. 1 or the football shape shown in FIGS. 4 and 7. Of course, in the next step, the occlusive assembly would be bonded to a one-piece pouch as shown in FIGS. 4 and 5 or a mechanical coupling member would be bonded to backing layer 32 as shown in FIG. 3. Because release paper 74 overlies release paper 72, the user is presented with a tab that can be gripped while sheet 74 is removed and the appliance is secured in place on the body. After adhesive layers 11 and 31 have been pressed onto the body, strip 72 is removed and the corner of adhesive layer 31 is pressed against the body. This construction avoids the need of slitting the release paper as done in prior adhesive systems.

Of course, the occlusive attching means of FIGS. 3, 4 and 5 can also be prepared by a conventional process in which component A is cut to shape, bonded to a sheet of component C, separate sheets of release paper are applied to adhesive surfaces 11 and 31, and the outline of component C and aperture 20 are cut and punched. This assembly is then bonded to the pouch wall as shown in FIG. 5 or a coupling member is affixed to backing layer 32 as shown in FIG. 3.

The occlusive attaching means of this invention as shown in FIGS. 1 and 2 is constructed by preparing adhesive layer 11 laminated between a sheet of release paper and polymeric backing film 12 as described above. The flange skirt 21 of the coupling member is then affixed to polymeric backing film by ultrasonic welding or other bonding technique. Component C is prepared by extruding relatively thin adhesive layer 31 onto backing layer material 32 while the other surface of adhesive layer 31 is covered with release paper. Component C is cut to the desired outer rectangular shape and a central opening is cut to fit component C around the periphery of rib 22 of the coupling member. At the same time a score cut is made to remove the release paper covering adhesive layer 31 in the area overlying flange skirt 21. Component C is then applied to the flange skirt 21 and the central starter hole 20 is punched out of component A. The bond between adhesive layer 31 and skirt 21 can be augmented by pretreating skirt 21 with corona discharge.

The occlusive attaching means of this invention as shown in FIG. 6 is constructed by preparing component A and C as described above. Component C is cut to the desired football shape and release paper on the portion of adhesive layer 31 overlying backing film 12 is removed. Component C is then bonded to backing film 12 and the assembly is sealed to the pouch by heat sealing pouch panel 42 to backing film 12. Pouch panel 41 is then heat sealed to panel 42 to complete the pouch.

Occlusive adhesive layers 11 and 31 are prepared by known methods of known formulas. Preferably, one or both adhesive layers are a blend on a weight percentage basis of about 40% polyisobutylene (available from Exxon as Vistanex® LM-MH) and about 60% of an equal weight mixture of pectin, gelatin, and sodium carboxymethylcellulose or one or both adhesive layers are a blend on a weight percentage basis of about 8% polyisobutylene (Vistanex® LM-MH), about 6% styrene-isoprene-styrene copolymer (such as Kraton® D 1107 available from Shell Chemical Co.), about 16.25% of butyl rubber (Exxon grade 065), about 12.75% tackifier (such as Pentalyn® H available from Hercules Chemical Co.), about 11.50% mineral oil, about 0.50% antioxidant, and about 45% of an equal weight mixture of pectin, gelatin, and sodium carboxymethylcellulose. Backing layer 32 and polymeric film layer 12, if present, are both preferably a 1 mil thick embossed low density polyethylene film.

While the occlusive attaching means of this invention has been described as part of a one or two-piece system, it should be appreciated that the occlusive attaching means such as that shown in FIG. 7 can also be employed as a separate dressing or skin barrier. The user would then adhesively secure a pouch to backing layer surface 32.

What is claimed is:

1. An occlusive dressing comprising a first adhesive componenet including a first moisture and stomal fluid occlusive adhesive layer of about 40 to about 100 mils thickness and a second adhesive component including a second moisture and stomal fluid occlusive adhesive layer of about 8 to about 20 mils thickness and a backing layer.

2. The occlusive dressing of claim 1 wherein said second adhesive component extends beyond said first adhesive component whereby said second adhesive layer contacts the skin beyond the area where said first adhesive component contacts the skin.

3. The occlusive dressing of claim 2 wherein said backing layer of said second adhesive component is a non-woven fabric.

4. The occlusive dressing of claim 2 wherein said backing layer of said second adhesive component is a thin polymeric film of about 1 to about 4 mils thickness.

5. The occlusive dressing of claim 2 wherein both occlusive adhesive layers are formulated from a blend comprising one or more water soluble or swellable hydrocolloids, and polyisobutylene, or a mixture of polyisobutylenes, or a mixture of one or more polyisobutylenes and one or more non-acrylic elastomers.

6. The occlusive dressing of claim 5 wherein one or both occlusive adhesive layers also includes one or more ingredients selected from mineral oil, tackifiers, and cohesive strengthening agents.

7. The occlusive dressing of claim 2 wherein said first occlusive adhesive layer is about 60 to about 80 mils thickness and said second occlusive adhesive is about 10 to about 12 mils thickness.

8. The occlusive dressing of claim 5 wherein one or both occlusive adhesive layers comprise on a weight percentage basis about 40% polyisobutylene, about 20% gelatin, about 20% pectin, and about 20% sodium carboxymethylcellulose.

9. The occlusive dressing of claim 6 wherein one or both occlusive adhesive layers comprise on a weight percentage basis about 8% polyisobutylene, about 6% styrene-isoprene-styrene copolymer, about 16.25% butyl rubber, about 12.75% tackifier, about 11.5% mineral oil, about 0.5% antioxidant, and about 45% of an equal weight mixture of pectin, gelatin, and sodium carboxymethylcellulose.

10. An occlusive attaching means for use as the body side of a two piece ostomy system comprising a first adhesive component including a first moisture and stomal fluid occlusive adhesive layer of about 40 to about 100 mils thickness and a thin polymeric backing film of about 1 to about 4 mils thickness, a coupling member including an upstanding rib and a flange, said flange secured to the backing film of said first adhesive component, and a second adhesive component comprising a second moisture and stomal fluid occlusive adhesive layer of about 8 to about 20 mils thickness and a backing layer, said second adhesive layer secured to the opposite surface of said coupling member flange and wherein said second adhesive component extends beyond the borders of said flange and said first adhesive component.

11. The occlusive attaching means of claim 10 wherein the backing layer of said second adhesive component is a non-woven fabric.

12. The occlusive attaching means of claim 10 wherein the backing layer of said second adhesive component is a thin polymeric film of about 1 to about 4 mils thickness.

13. The occlusive attaching means of claim 10 wherein both occlusive adhesive layers are formulated from a blend comprising one or more water soluble or swellable hydrocolloids, and polyisobutylene or a mixture of polyisobutylenes, or a mixture of one or more polyisobutylenes and one or more non-acrylic elastomers.

14. The occlusive attaching means of claim 13 wherein one or both occlusive adhesive layers also include one or more ingredients selected from mineral oil, tackifiers, and cohesive strengthening agents.

* * * * *